United States Patent [19]
Baerts

[11] Patent Number: 5,614,682
[45] Date of Patent: Mar. 25, 1997

[54] SAMPLING DEVICE FOR MOLTEN METALS

[75] Inventor: Christiaan E. E. Baerts, Paal, Belgium

[73] Assignee: Heraeus Electro-Nite International N.V., Houthalen, Belgium

[21] Appl. No.: 540,284

[22] Filed: Oct. 6, 1995

[30] Foreign Application Priority Data

Nov. 14, 1994 [DE] Germany .......................... 44 40 577.4

[51] Int. Cl.$^6$ ...................................................... G01N 1/12
[52] U.S. Cl. ..................................... 73/864.58; 73/864.55
[58] Field of Search ........................... 73/864.53–864.59, 73/DIG. 9

[56] References Cited

U.S. PATENT DOCUMENTS

| | | | |
|---|---|---|---|
| 3,646,816 | 3/1972 | Hance et al. | 73/DIG. 9 X |
| 3,656,347 | 4/1972 | Collins | 73/DIG. 9 X |
| 3,913,404 | 10/1975 | Boron | 73/DIG. 9 X |
| 4,361,053 | 11/1982 | Jones et al. | 73/864.53 |
| 4,699,014 | 10/1987 | Boron | 73/864.57 |
| 5,033,320 | 7/1991 | Baerts | 73/864.57 X |
| 5,415,052 | 5/1995 | Baerts | 73/864.53 X |

FOREIGN PATENT DOCUMENTS

| | | |
|---|---|---|
| 0107219A1 | 5/1984 | European Pat. Off. . |
| 2043496 | 11/1971 | Germany . |
| 3000201C2 | 7/1981 | Germany . |
| 214441 | 10/1984 | Germany . |
| 285190A5 | 12/1990 | Germany . |
| 3919362A1 | 12/1990 | Germany . |
| 4130400A1 | 3/1993 | Germany . |

*Primary Examiner*—Thomas P. Noland
*Attorney, Agent, or Firm*—Panitch Schwarze Jacobs & Nadel, P.C.

[57] ABSTRACT

A sampling device for molten metals with a sample chamber arranged in a paperboard tube has an inflow canal leading through the paperboard tube, the canal being formed essentially of a heat-resistant inflow tube, such that the outer end of the inflow tube ends below (inside) the outer circumference of the sampling device and is closed off by a delayed-action device. In order to create a sampling device in which the intrusion of contaminants into the sample chamber is prevented, especially slag particles, gas occlusion particles and particles of the paperboard tubes, the delayed-action device is constructed as a multi-layered cap, whereby between cap and paperboard tube an intermediate space is formed, which is filled with cement.

8 Claims, 2 Drawing Sheets

SAMPLING DEVICE FOR MOLTEN METALS

FIELD OF THE INVENTION

The invention concerns a sampling device for molten metals with a specimen chamber positioned in a paperboard tube, and having an inflow canal passing through the paperboard tube the canal being made essentially of a heat-resisting intake tube, in which the outer end of the inflow tube ends below (inside) the outer circumference of the sampling device and is closed off with a delayed-action device.

BACKGROUND OF THE INVENTION

An apparatus of this type, in which the inlet in the casing surface of the paperboard tube opens into the sample chamber, is known from DE-PS 30 00 201. A sampling device is there described in which the sample chamber has a lateral inlet for molten metals. The inlet opening terminates at the casing surface of the paperboard tube surrounding the sample chamber and is encased with a covering which forms a delayed-action device and closes off the inlet opening during the immersion process of the sampling device into the molten metal, so that when penetrating the slag layer an intrusion of contaminating particles into the chamber is prevented. The delayed-action device is destroyed after penetrating the slag layer and the inlet opening becomes accessible. The intrusion of slag during penetration through the slag layer is of course prevented by such a closure, but intrusion cannot be prevented through the then opened inlet of other types of contamination, as for example, gas bubbles or particles from the side covering intrude into the chamber and contaminate the sample.

SUMMARY OF THE INVENTION

Proceeding from this state of the art, it is an object of the invention to create a sampling device of the above-mentioned type, in which the intrusion of contamination is prevented, particularly from slag particles, gas occlusion particles and particles of the paperboard tube, into the sample chamber.

The problem is solved according to the invention in that the delayed-action device is constructed as a multi-layered cap, in which an interspace formed between the cap and the paperboard tube is filled with cement. By an arrangement of this type the inlet opening is not only protected against mechanical damage, since it does not protrude beyond the paperboard tube—geometry, but it is also ensured that the cap closing the inflow tube is exposed to the heat load only on its front end during the immersion into the molten metal. Further, the contamination particles possibly fastening themselves to the outer layer of the cap are flushed away from the inlet opening during the dissolution of this layer and before the destruction of the inner layer of the cap, so that these contamination particles cannot invade the sample chamber after destruction of the cap. The multi-layered cap is not only capable of being pre-assembled according to the individual respective requirements and fixed as one piece at the outer end of the inflow canal, it also seals off the inlet canal by means of the cement to such an extent, that a gas-tight closure is formed between the molten metal and the sample chamber, so that the normal pressure will be maintained in the inflow canal and in the sample chamber until the cap is destroyed.

In addition, in order to ensure the gas-tightness, it is expedient that the cement seal off a gap formed between the cap and the inflow tube. Furthermore, it is advantageous that the multi-layered cap have a metal cap, onto the outer end face of which is adhered a delayed action disc of cardboard, wood or a similar combustible material, that a metal foil borders on the outer surface of the delayed action disc, and that a metal layer is positioned between the lateral face of the delayed action disc and the cement. A layered construction of this type can be made very simply and assures that the inflow canal is opened only after penetrating the slag layer and clearing away the contamination particles. Thus, after penetrating the slag layer, the delayed action disc is burned away, which thereby prevents a rapid destruction of the metal cap. On the other hand, the delayed action disc is protected from the heat radiation on the approach of the sampling device to the molten metal by the metal foil, since this heat is, for the most part, reflected by the metal foil. The metal foil is destroyed on entering the slag layer. Since the multi-layered cap is fastened on the sides with cement, which is poured in a wet state between the cap and the paper board tube, a metal layer protects the delayed action disc against destruction by means of the moisture escaping from the cement.

It is expedient that the metal layer be made of a metal casing, which is adjacent to the lateral face of the metal cap and whose outer edge is bent inward and lies against a part of the metal foil. This type of an arrangement assures a firm seating of the delayed action disc on the metal cap, during and after the installation, since it is clamped between the metal cap and the metal casing. The metal casing guarantees a high stability of the multi-layered cap without constricting the inlet opening in its cross-section in an adverse manner, since the end of the cap in front of the metal casing is essentially uncovered, but this end face is naturally covered by the essentially thinner metal foil, which is destroyed on entrance into the slag layer or into the molten metal.

It is expedient that within the metal cap is arranged a second metal cap. The possibility is thereby presented of using, with equal protective effect, essentially thinner metal caps with an essentially lesser mass and hence a lower heat capacity. During the destruction of the first metal cap a gas filled intermediate space is formed between the two caps which causes an eddying effect in the melt striking the second metal cap, so that contamination possibly encroaching against the second metal cap is swept away. As a result neither contamination of a solid type nor gas bubbles from the fluid metal can invade the inflow canal. It is advantageous for flawless sampling that only the end face of the multi-layered cap be essentially free of cement. On the one hand, this prevents the melt from entering the inflow canal laterally through the metal cap, and on the other hand assures that the end face of the multi-layered cap has no incombustible materials, which could hinder the resulting layer-wise destruction of the end face of the cap or which could penetrate into the sample chamber after opening of the inflow canal.

Preferably, the delayed action disc is made of cardboard and the metal foil of aluminum. These materials assure a simple manufacturability and a flawless operation of the multi-layered cap, since after penetration of the sampling device into the molten metals, especially into molten steel in a satisfactory manner, both materials are easily destroyed.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF PREFERRED EMBODIMENTS

Figure 1:
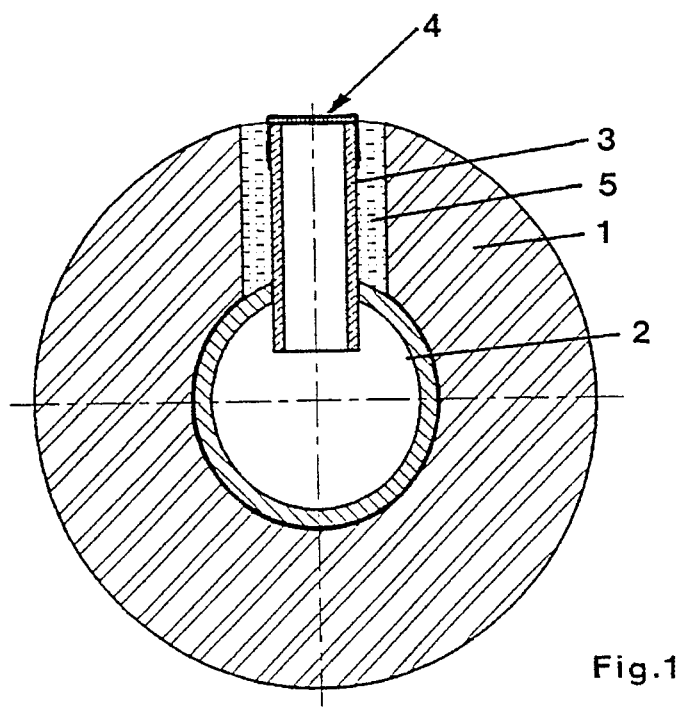
FIG. 1 is a cross-section through the sampling device.

One embodiment of the sampling device according to the invention is shown in cross-section in FIG. 1. In a paperboard tube 1 a sample chamber 2 is concentrically arranged. An inflow tube 3 projects into the sample chamber 2 and leads through an opening in the paperboard tube 1 to below (inside) the outer diameter of the paperboard tube 1. The inflow tube 3 is closed at its outer end with a multi-layered cap 4 and fixed in the paperboard tube 1 with a refractory cement 5, whereby the cement 5 ensures a gas-tight seal between the paperboard tube 1 and the inflow tube 3, as well as between the inflow tube 3 and the multi-layered cap 4. The outer face of the multi-layered cap 4 is arranged approximately in the outer surface of the paperboard tube 1.

Figure 2:
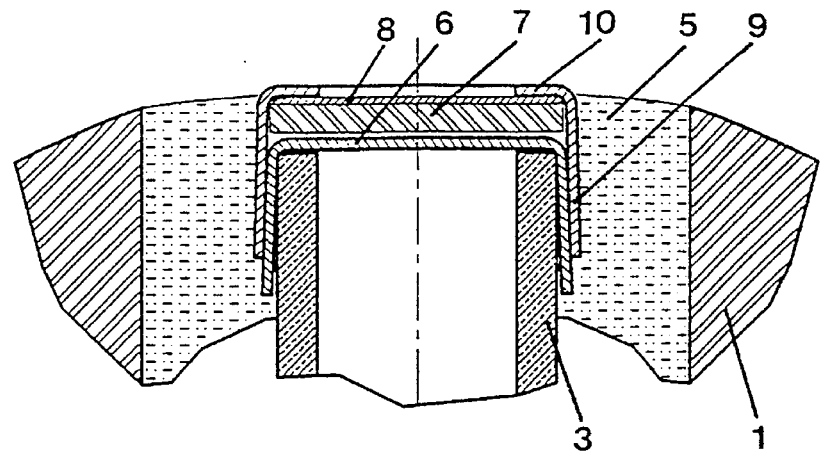
FIG. 2 is a schematic representation of the inflow canal with a multi-layered cap.

FIG. 2 shows the construction of a multi-layered cap, as suitable for a thermal analysis sampling unit. The multi-layered cap includes a metal cap 6, for instance of iron, which has a thickness of about 0.2 mm. This metal cap 6 lies at least partially against the inflow tube 3, possible gaps between the intake tube 3 and the metal cap 6 being filled with cement 5. The inflow tube 3 is made of quartz and has an inside diameter of about 12 mm. On the top (outside) of the metal cap 6 is adhesively attached a delayed action disc 7 made of cardboard. This adhesive connection assures a good contact and a firm seating of the delayed action disc 7 on the metal cap 6. The thickness of the delayed action cap 7, depending on the intended delay, lies between about 0.5 and 3 mm, also depending on the temperature of the melt and the diameter of the delayed action disc 7.

The delayed action disc 7 is provided on its outer surface with a closely fitting metal foil 8 for reflecting heat radiation. The metal foil can preferably be made of aluminum. Over the metal cap 6 with the delayed action disc 7 and the metal foil 8 a metal casing 9 is positioned, in such a way that the lateral wall of the metal casing 9 lies against the lateral wall of the metal cap 6, and the outer rim 10 of the metal casing 9 is bent inward, so that it lies against the metal foil 8 on its outer rim and the upper surface of the metal foil is left essentially uncovered. As a result, the opening of the inflow tube 3 is not reduced essentially by the metal casing 9. As a result, the opening of the inflow tube 3 is essentially not decreased by the metal casing 9.

Just as the metal cap 6, the metal casing 9 is made of iron with a thickness of about 0.2 mm. In the intermediate space between the inflow tube 3 and the multi-layered cap as well as the paperboard tube cement 5 is positioned, so that cement 5 and rim 10 form a roughly level surface with the paperboard tube 1. The metal casing 9 assures by its positioning a precise isolation of the delayed action disc 7 against moisture on pouring cement 5, so that the delayed action disc 7 is not prematurely destroyed during the construction of the sampling device. The multi-layered cap is prefabricated as such and is installed as a whole unit onto the intake tube 3.

Figure 3:
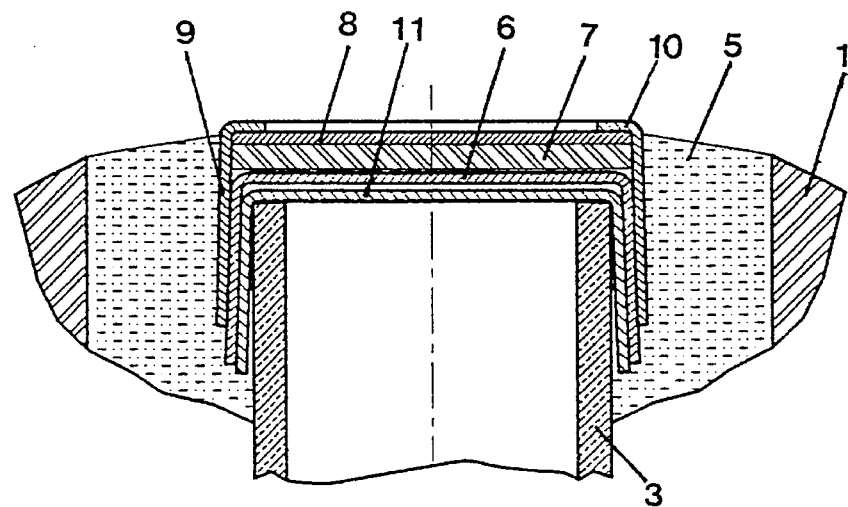
FIG. 3 is a schematic representation of the inflow canal with two metal caps arranged one over the other.

In FIG. 3 is shown a similar sampling device. In contrast to the arrangement shown in FIG. 2, a second metal cap 11 is positioned directly on the inflow tube 3 inside of the metal cap 6. The inside diameter of the inflow tube 3 in this example is about 16 mm; also the second metal cap 11 is made of about 0.2 mm thick iron. Both caps are pressed one onto the other; there exists a small airspace between the facing ends of the metal cap 6 and the second metal cap 11. On immersion of the sampling device into the melt the airspace expands, providing an additional delay in the inflow of the molten metal into the sample chamber 2. As already described above, it also provides that contamination particles and gases are swept away prior to the destruction of the second metal cap 11, so that they cannot enter into the sample chamber 2.

It has been shown, for example, that the delayed action period by means of a delayed action disc 7 with a thickness of 1 mm and a diameter of about 20 mm at a molten metal temperature between 1560° C. and 1700° C. is about 1–4 seconds. The multi-layered cap represented in FIG. 3 is used predominantly in sampling for test analyses in which the molten metals in the sample chamber may possibly contain slightly volatile elements.

Figure 4:
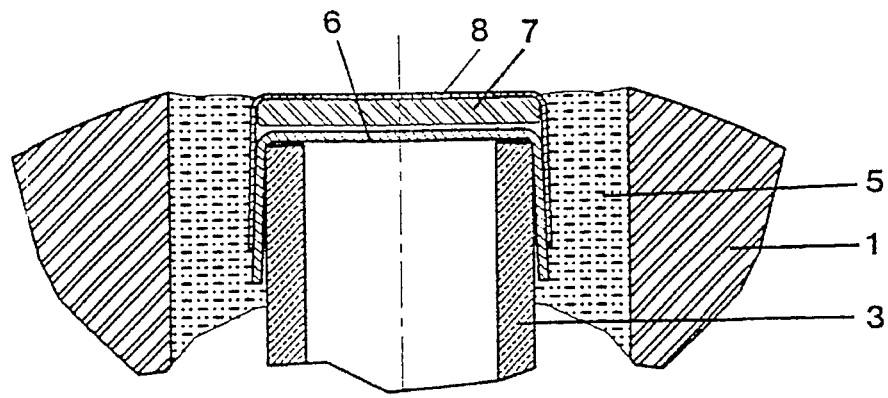
FIG. 4 is a schematic representation of a multi-layered cap in a simplified construction form.

In FIG. 4 is shown a multi-layered cap in which, in contrast to the arrangement shown in FIG. 2, the metal casing 9 and the metal foil 8 form a unit, such that the metal foil 8 is constructed as the cap, whose side wall lies against the side wall of metal cap 6.

It will be appreciated by those skilled in the art that changes could be made to the embodiments described above without departing from the broad inventive concept thereof. it is understood, therefore, that this invention is not limited to the particular embodiments disclosed, but it is intended to cover modifications within the spirit and scope of the present invention as defined by the appended claims.

I claim:

1. A sampling device for molten metals comprising a sample chamber (2) arranged in a paperboard tube (1) and having an inflow canal leading through the paperboard tube, the inflow canal comprising a heat-resisting inflow tube (3), an outer end of the inflow tube terminating inside an outer circumference of the sampling device and being closed with a delayed-action device, the delayed-action device comprising a multi-layered cap (4), and an intermediate space between cap (4) and paperboard tube (1) being filled with cement (5), wherein the multi-layered cap (4) comprises a metal cap (6), on whose outside end face is adhered a delayed action disc (7) made of combustible material, wherein a metal foil (8) lies against an outer surface of the delayed action disc (7), and wherein between a lateral surface of the delayed action disc (7) and the cement (5) is positioned a metal layer.

2. The sampling device according claim 1, wherein the cement (5) seals any gap formed between the cap (4) and the inflow tube (3).

3. The sampling device according to claim 1, wherein the metal layer comprises a metal casing (9) adjacent to a lateral surface of the metal cap (6), an outer edge (10) of the metal layer being bent inward and lying against a part of the metal foil (8).

4. The sampling device according to claim 1, wherein within the metal cap (6) is arranged a second metal cap (11).

5. The sampling device according to claim 1, wherein only an end surface of the multi-layered cap (4) is essentially free of cement.

6. The sampling device according to claim 1, wherein the delayed action disc (7) comprises cardboard and the metal foil (8) comprises aluminum.

7. The sampling device according to claim 1, wherein the delayed action disk 7 comprises wood.

8. The sampling device according to claim 1, wherein the delayed action disk (7) comprises cardboard.

* * * * *